… …

United States Patent [19]

Mawhirt et al.

[11] Patent Number: 5,584,846
[45] Date of Patent: Dec. 17, 1996

[54] LOW COST DISPOSABLE LANCET

[75] Inventors: James A. Mawhirt, Brooklyn, N.Y.; Anthony F. Kuklo, Jr., Bridgewater; Donald Foggia, Ocean, both of N.J.

[73] Assignee: International Technidyne Corporation, Edison, N.J.

[21] Appl. No.: 549,173

[22] Filed: Oct. 27, 1995

[51] Int. Cl.⁶ .................................................. A61B 17/32
[52] U.S. Cl. ............................................ 606/181; 606/182
[58] Field of Search .................................. 606/182, 180, 606/188

[56] References Cited

U.S. PATENT DOCUMENTS 3,659,608  5/1972  Perry ........................................ 606/182

*Primary Examiner*—Michael Powell Buiz
*Assistant Examiner*—Mark S. Leonardo
*Attorney, Agent, or Firm*—Plevy & Associates

[57] ABSTRACT

A low cost lancet device for creating a skin incision. The lancet contains a unistructurally formed plastic body, thereby making the lancet device easy to manufacture at low cost. The plastic body contains a resilient spring loop that attaches an arm element to an opposing base element. The spring loop is curved, therefore the arm element is retained above the base element by the spring loop. A blade is disposed on the arm element. The blade aligns with a slot in the base element so that when the spring loop is compressed, and the arm element is moved toward the base element, the blade extends through the slot in the base element. A protrusion extends from the base element that obstructs the movement of the arm element toward the base element. As a result, when a force is applied to the arm element, the arm element abuts against the protrusion and applies a bias to the protrusion that acts to displace the protrusion. When a predetermined threshold force is applied to the arm element, the arm element moves past the obstructing protrusion and the arm element rapidly moves toward the base element, compressing the spring loop. As the arm element approaches the base element, the blade on the arm element extends through the slot in the base element and creates the desired incision. Once the applied force is removed from the arm element, the bias of the spring loop moves the arm element away from the base element, thereby retracting the blade back through the slot in the base element.

19 Claims, 3 Drawing Sheets

LOW COST DISPOSABLE LANCET

BACKGROUND OF THE INVENTION

I. Field of the Invention

The present invention relates to disposable lancet devices used to create an incision in the skin of a patient, through which a blood sample can be obtained. More particularly, the present invention relates to low cost lancet devices that are easy and inexpensive to both manufacture and assemble.

II. Statement of the Prior Art

Blood samples are drawn routinely from patients for use in numerous types of blood tests. The blood needed for many tests is conventionally drawn by creating a small incision in the patient's skin. Typically, such incisions are made on the patient's fingertip, However, with patients such as neonates or persons with poor circulation, the incision can be made in alternate areas such as the foot, arm or leg. Typically, the device used to create the needed incision in the patient is a mechanical lancet device. Such lancet devices conventionally employ a cutting blade spring loaded within a housing. The housing is placed against a patient's skin and the blade is released. The potential energy stored within the spring bias of the blade then causes the blade to exit the housing and to create the needed incision in the patient's skin. The advantage of such mechanical lancet devices is that uniform incisions can be made providing good control over the location, depth and sterility of the incision. Furthermore, such mechanical lancet devices often prevent the patient from seeing the often unsettling scene of his or her skin actually being cut.

In the development of the art for mechanical lancet devices, many different designs have been created. The most modern of the designs typically are disposable, having retractable blades and other operations that prevent their reuse after a single incision has been made. Another common feature to many prior art lancet devices is that they make incisions using a plunge cut, that is the cutting blade is plunged through the skin traveling perpendicular to the skin and the size of the incision matches the size of the cutting blade. Such prior art lancets are exemplified by U.S. Pat. No. 5,133,730 issued on Jul. 28, 1992 to Biro, entitled DISPOSABLE RETRACTABLE FINGER STICK DEVICE AND METHOD FOR MAKING THE SAME and assigned to International Technidyne Corporation the assignee herein. In the Biro patent, a sharp blade on a pivot arm is spring biased to move out of, and then reenter, a housing via an orifice in the housing. Although the blade is positioned on a pivot arm, the blade is directed into the skin of the patient relatively perpendicular to the surface of the skin. The shape of the blade helps the blade enter the skin and make the needed incision.

Other lancet devices that create a plunge cut are exemplified by U.S. Pat. No. 3,760,809 to Cambell, Jr. entitled SURGICAL LANCET HAVING CASING and U.S. Pat. No. 5,395,388 to Schrage, entitled SINGLE UNIT LANCET DEVICE. Since lancet devices are typically designed to be disposable after one use, it will be understood that the manufacturer with the lowest unit price would have an advantage over competitors. Consequently, manufactures have been motivated to design disposable lancets with simpler designs that can be made less expensively. In response to such design efforts, manufactures have developed lancets with only two or three separate parts. In such devices a cutting blade is held by a complex molded structure that both advances and retracts the blade. Such prior art is exemplified by U.S. Pat. No. 4,553,541 to Burns, entitled AUTOMATIC RETRACTABLE LANCET ASSEMBLY, and U.S. Pat. No. 5,212,879 to Biro et al., entitled METHOD FOR MANUFACTURING A DISPOSABLE-RETRACTABLE FINGER STICK DEVICE, which is assigned to International Technidyne Corp., the assignee herein. Although such devices have far less parts than some prior art lancet devices, they are no less complex. Accordingly, the tools needed to mold the primary lancet structure is highly complex and the parts produced must be maintained at high tolerances. This produces a large amount of reject parts and significant downtime as the molding tool is cleaned and maintained. All this work adds to the cost of the lancet device and makes it difficult to consistently produce a high quality product.

In many prior art lancet devices, expensive metal springs are used, wherein the cutting blade is either part of the spring or is driven by the spring. The use of springs adds significantly to the cost of the overall lancet as well to the complexity of assembling the lancet with the spring being in its compressed, ready-to-use orientation.

It is therefore an object of the present invention to provide a lancet device that does not use a metal spring.

It is a further object of the present invention to provide a disposable lancet that is relatively inexpensive to manufacture and not requiring complex and molded parts.

SUMMARY OF THE INVENTION

The present invention is a low cost lancet device for creating a skin incision. The lancet is formed from a unistructurally molded plastic body, thereby making the lancet device easy to manufacture at low cost. The plastic body contains a resilient spring loop that attaches an arm element to an opposing base element. The spring loop is curved, therefore the arm element is retained above the base element by the spring loop. A blade is either attached to, or formed as part of, the arm element. The blade aligns with a slot in the base element so that when the spring loop is compressed, and the arm element is moved toward the base element, the blade extends through the slot in the base element.

Before the lancet device is used, a protrusion extends from the base element that obstructs the movement of the arm element toward the base element. As a result, when a force is applied to the arm element, the arm element abuts against the protrusion and applies a bias to the protrusion that acts to displace the protrusion. When a predetermined threshold force is applied to the arm element, the arm element moves past the obstructing protrusion and the arm element rapidly moves toward the base element, compressing the spring loop. As the arm element approaches the base element, the blade on the arm element extends through the slot in the base element and creates the desired incision. Once the applied force is removed from the arm element, the bias of the spring loop moves the arm element away from the base element, thereby retracting the blade back through the slot in the base element.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Figure 1:
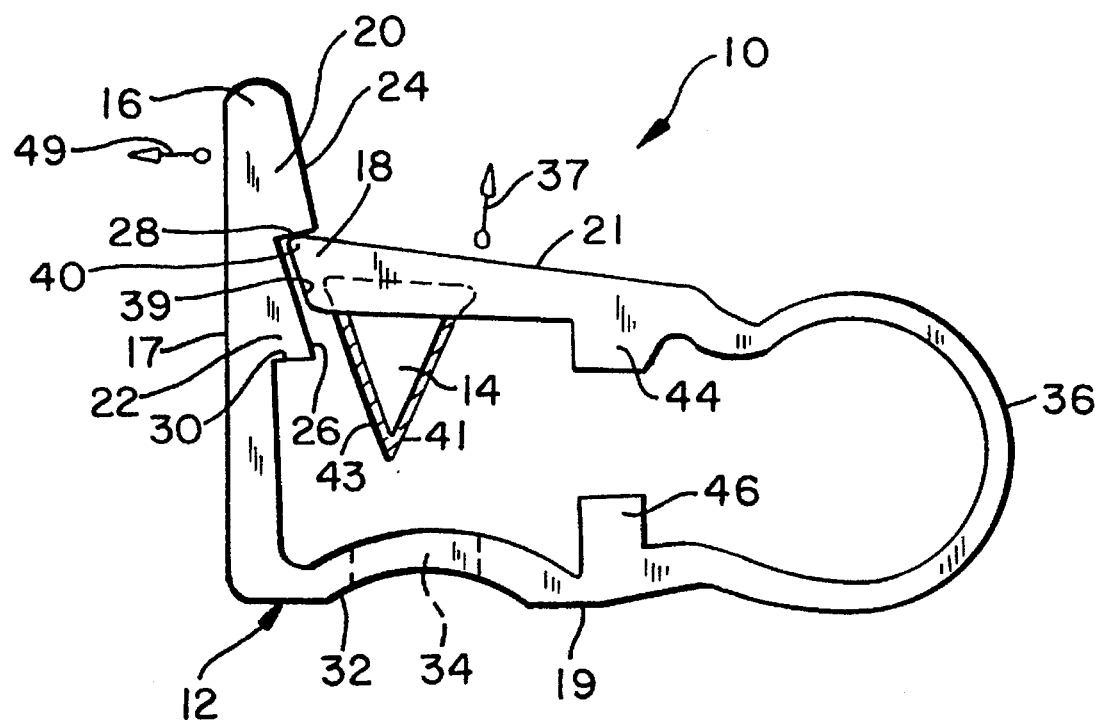
FIG. 1 is a side view of one preferred embodiment of the present invention lancet device shown in an unused condition, ready to be used on a patient.

Referring to FIG. 1, the present invention lancet device 10 is shown in a set, unused condition, wherein the lancet device 10 is ready to create a skin incision in the manner to be later explained. In the shown embodiment, the lancet device 10 is comprised essentially of only two parts, those parts being the plastic body 12 and the cutting blade 14. However, in an alternate embodiment, the blade can be molded as part of the plastic body, thereby producing a lancet from a single molded piece. In FIG. 1, the plastic body 12 is a single elongated element having a first end 16 and a second end 18, wherein the elongated element is molded along a complex path that provides the plastic body 12 with a functional configuration needed for the operation of the lancet device. The plastic body 12, although unistructurally formed, contains four main sections. Those sections include a vertical section 17 proximate the first end 16, a base section 19, an arm section 21 proximate the second end 18 and a spring loop 36 connecting the arm section 21 to the base section 19.

Two protrusions 20, 22 are disposed on a vertical section 17 of the plastic body 12, near the first end 16. Each of protrusions 20, 22 are shaped as serrations having a sloped surface 24, 26 that sloped downwardly toward first end 16. A detent surface 28, 30 is provided at the ends of each protrusion 20, 22, where the sloped surface 24, 26 ends abruptly. A predetermined length below the detent surface 30 of the second protrusion 22, the vertical section 17 ends as the plastic body 12 turns at approximately a right angle and leads into the base section 19. An arcuate indent 32 is formed in the base section 19 proximate the right angle turn. The arcuate indent 32 is sized to receive the curved surface of a fingertip therein. A slot 34 is disposed in the plastic body 12 at the apex of the arcuate indent 32. As will later be explained, the cutting blade 14 passes through the slot 34 to create an incision in any fingertip held within the arcuate indent 32.

At the end of the base section 19, the plastic body 12 is formed into a resilient spring loop 36. The bias provided by the curved spring loop 36 biases the arm section 21 of the plastic body 12 in the direction of arrow 37 as the spring loop 36 tries to open into a more flat orientation. The second end 18 of the plastic body 12, at the end of the arm section 21 opposite the spring loop 36, has an angled surface 39 that extends to a salient point 40. In the shown embodiment, the salient point 40 at the second end 18 of the plastic body 12 is in abutment with the detent surface 28 of protrusion 20 near the first end 16 of the plastic body 12. The bias of the spring loop 36, acting in the direction of arrow 37, biases the salient point 40 against the detent surface 28 which retains the second end 18 in a set position.

In the preferred embodiment, the blade 14 is pointed having two sharpened edges 41, 43 that meet at a common point. In the shown embodiment, the blade 14 is a separate metal piece that is joined to the plastic body 12. The blade 14 passes into a slit 42 formed in the arm section 21 of the plastic body 12, wherein the blade 14 engages the plastic body 12 with an interference fit. In a first alternate embodiment, a metal cutting blade can be directly molded into the material of the plastic body or be otherwise mechanically or adhesively anchored. In a second alternate embodiment, the blade can be made of plastic and can be unistructurally molded as part of the plastic body 12. As such, no assembly of separate components would be required.

Two stop protrusions 44, 46 are also formed as part of the plastic body 12 on opposite sides of the spring loop 36. When oriented in the configuration of FIG. 1, the two stop protrusions 44, 46 align with one another, and are separated by the spring bias of the spring loop 36.

Figure 2:
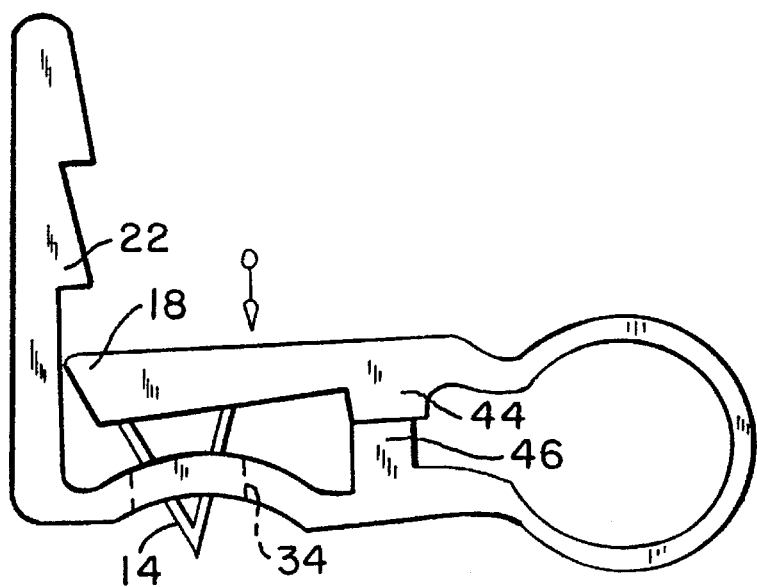
FIG. 2 is a side view of the embodiment of the lancet device presented in FIG. 1, shown during use when a blade extends from the lancet device to create an incision.

To operate the lancet device 10, the lancet device 10 is placed against a person's finger so that the arcuate indent 32 abuts the skin of the finger in the area where the incision is to be made. A predetermined force is then applied to the arm section 21 of the plastic body 12 above the cutting blade 14. Once the applied force overcomes the opposite force supplied by the bias of the spring loop 36, the second end 18 of the plastic body 12 is pushed into abutment against the sloped surface 26 of the second protrusion 22. As the angled surface 39 of the second end 18 is pushed against the sloped surface 26 of the second protrusion 22, a wedge action is produced that biases the vertical section 17 of the plastic body 12 in the direction of arrow 49. As the angled surface 39 of the second end 18 rides further along the sloped surface 26 of the second protrusion 22, the resistance to further advancement increases as the vertical section 17 increasingly resists further deformation from its original vertical orientation. Eventually, the second end 18 of the plastic body 12 passes over the sloped surface 26 of the second protrusion 22, whereby the resistance to movement caused by the wedge action between the angled surface 39 and the sloped surface 26 is suddenly eliminated. Referring to FIG. 2, it can be seen that as the second end 18 of the plastic body 12 moves past the second protrusion 22, the excess energy created by the sudden release of resistance causes the cutting blade 14 to rapidly descend and extend through the slot 34. The rapid advancement of the cutting blade 14 is stopped by the abutment of the two stop protrusions 44, 46 against one another. As such, it will be understood that the distance at which the cutting blade 14 will extend through the slot 34 depends upon both the length of the cutting blade 14 and the length of the stop protrusions 44, 46.

Figure 3:
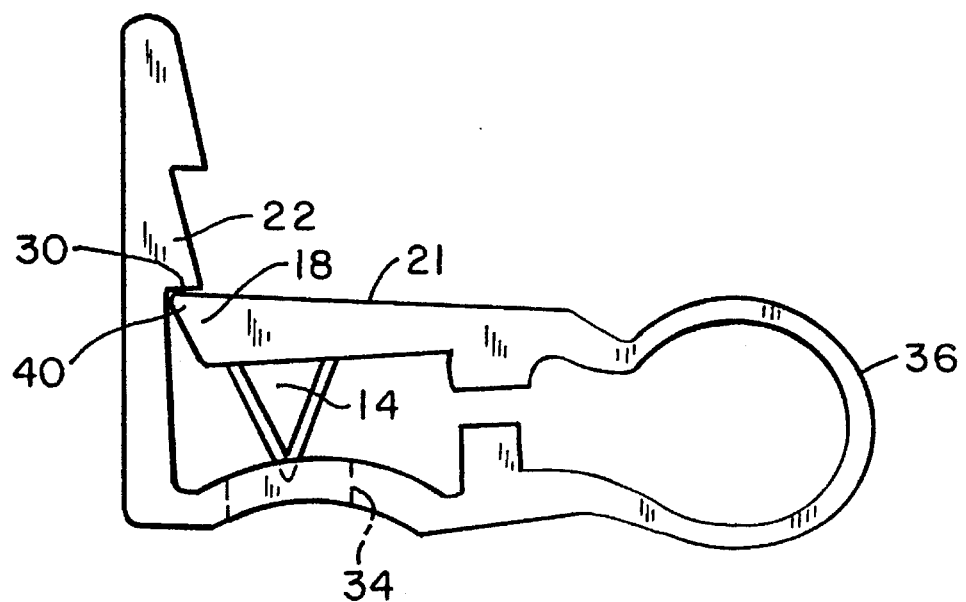
FIG. 3 is a side view of the embodiment of the lancet device presented in FIG. 1 and FIG. 2, shown after use, wherein the blade has been retracted.
Figure 4:
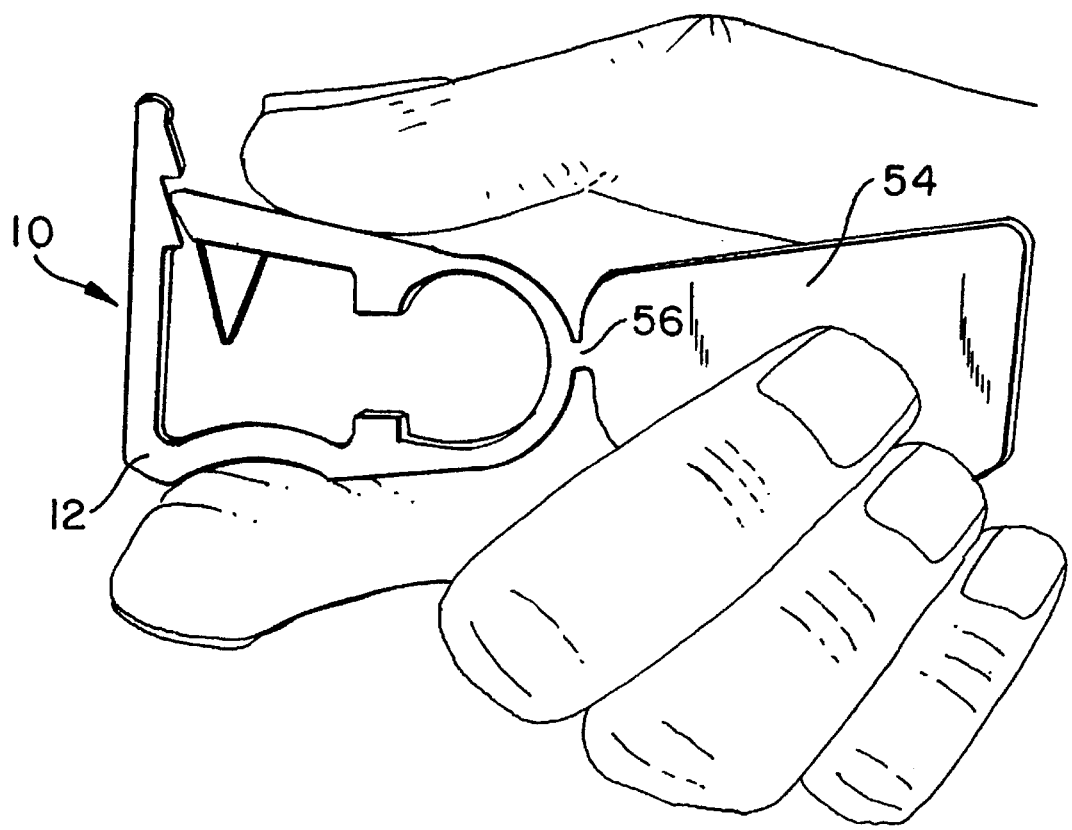
FIG. 4 is a side view of an alternate embodiment of the present invention lancet containing a protective side panel that can be selectively used as a handle.

Referring to FIG. 3, it can be seen that as the downward force is removed from the arm section 21, the spring bias of the spring loop 36 again moves the second end 18 of the plastic body 12 upwardly until the salient point 40 at the tip of the second end 18 abuts against the detent surface 30 of the second protrusion 22. The action of the spring loop 36 retracts the cutting blade 14 back through the slot 34 so that the cutting blade 14 no longer extends into the area of the arcuate indent 32. It will therefore be understood that the length of blade 14 should be no longer than the length between the detent surface 30 of second protrusion 22 and the bottom of the slot 34 in the arcuate indent.

In order to help keep the cutting blade 14 sterile and to prevent accidental contact with the cutting blade 14, the present invention lancet device 10 may optionally come equipped with a removable side panel. In one embodiment, a paper panel (not shown) can be used and may be adhesively coupled to the side of the lancet device, thereby preventing a person from accidentally contacting the cutting blade. The paper panel would include a pull tab that enables the panel to be readily pulled away from the side of the lancet device, prior to use.

In the shown embodiment, a preferred plastic panel 54 is shown. The plastic panel 54 can be integrally molded as part of the plastic body 12 of the lancet device 10. A living hinge 56 is molded at the junction between the plastic panel 54 and the plastic body 12, thereby enabling the plastic panel 54 to be folded back prior to the use of the lancet device 10. Initially, the plastic panel 54 covers the open side of the lancet device 10, thereby protecting the lancet device 10 from being accidentally activated. The plastic panel 54 also prevent a person from accidentally touching the cutting blade 14. In the shown embodiment, it can be seen that when the lancet device 10 is ready for use, the plastic panel 54 is rotated about the living hinge 56 approximately 180 degrees, wherein the plastic panel 54 no longer protects the cutting blade 14, but now rather acts as a handle. In the folded position, the plastic panel 54 doubles the overall length of the lancet device 10, thereby making the lancet device 10 easier to grasp. The grasping of the plastic panel 54 like a handle also prevents the lancet device 10 from accidently turning if compressed with an off-center force. Although the shown embodiment only illustrates one plastic side panel, it will be understood that two side panels can be used, wherein one panel covers each side of the lancet device.

It will be understood that the embodiment of the present invention lancet described herein is merely exemplary and a person skilled in the art may make variations and modifications without departing from the spirit and scope of the invention. All such variations and modifications are intended to be included within the scope of the invention as defined by the appended claims.

What is claimed is:

1. A lancet device comprising:

a base element having a top surface and a bottom surface;

an arm element coupled to said base element by a spring element, wherein said arm element can be selectively moved relative said base element between a first position and a second position;

a blade affixed to said arm element, wherein said blade is supported above said top surface of said base element when said arm element is at said first postion and said blade extends past said bottom surface of said base element when said arm element is at said second position; and resistive means for resisting the movement of said arm element from said first position to said second position until a predetermined force in excess of a threshold value is applied to said arm element that biases said arm element toward said second position;

wherein said spring element biases said arm element into said first position to maintain said blade above said top surface of said base element.

2. The device according to claim 1, wherein said base element, said arm element and said spring element are molded as part of a single unistructural body.

3. The device according to claim 2, wherein said blade is molded as part of said unistructural body.

4. The device according to claim 1, wherein a first stopping protrusion extends from said top surface of said base element and a second stopping protrusion extends from said arm element, wherein said first stopping protrusion and said second stopping protrusion abut against each other when said arm element is at said second position, thereby separating said arm element from said top surface of said base element by a predetermined distance.

5. The device according to claim 1, wherein said a slot is disposed in said base element, said blade extending through said slot when said arm element is at said second position.

6. The device according to claim 1, wherein an arcuate relief is disposed on said bottom surface of said base element, said arcuate relief being sized to receive a portion of a finger therein, wherein said blade extends past said bottom surface of said base element in said arcuate relief when said arm element is at said second position.

7. The device according to claim 1, wherein said resistive means includes a protrusion extending from said base element, wherein said arm element abuts against said protrusion when said arm element is at said first position and said protrusion initially obstructs movement of said arm element from said first position to said second position, said arm element displacing said protrusion out of contact with said arm element when said predetermined force is applied to said arm element.

8. The device according to claim 1, wherein said arm element is joined to said base element by said spring element.

9. The device according to claim 1, further including at least one removable side panel that extends in a first orientation between said arm element and said base element when said arm element is at said first position, whereby said at least one side panel protects said blade prior to use.

10. The device according to claim 9, wherein said at least one panel is selectively positionable between said first orientation and a second orientation where said side panel extend away from said base element and acts as a handle to facilitate grasping said device.

11. A lancet device comprising:

an elongated member having a first end, a second end, and a curved section which turns said second end back toward said first end such that said second end terminates at a point over a predetermined region of said elongated member between said first end and said second end, wherein said second end can be resiliently deformed from a first position, a predetermined distance away from said predetermined region, to a second position closer to said predetermined region;

a slot disposed in said predetermined region of said elongated member; and a blade coupled to said elongated member proximate said second end, wherein said blade extends through said slot when said second end is at said second position;

wherein said curved section biases said second end into said first position to maintain said blade said predetermined distance away from said predetermined region of said elongated member.

12. The device according to claim 11, further including resistive means for resisting the movement of said second end from said first position to said second position until a predetermined force in excess of a threshold value is applied to said second end that acts to bias said second end toward said second position.

13. The device according to claim 11, further including a first stopping protrusion extending from said elongated member on a first side of said curved region and a second stopping protrusion extending from said elongated member on an opposite second side of said curved section, wherein said first stopping protrusion abuts against said second stopping protrusion when said second end is at said second position.

14. The device according to claim 12, wherein said elongated member is configured so that said second end of said elongated member abuts against said first end of said elongated member when said second end is at said first position.

15. The device according to claim 14, wherein said resistive means includes a protrusion extending from said elongated member proximate said first end, and said second end of said elongated member abuts against said protrusion when said second end is at said first position, wherein said protrusion initially obstructs movement of said second end from said first position to said second position, said second end displacing said protrusion out of contact with said second end when said predetermined force is applied.

16. The device according to claim 11, wherein said elongated member is unistructurally formed of plastic.

17. The device according to claim 11, further including at least one handle element coupled to said curved region of said elongated member.

18. The device according to claim 17, wherein said at least one handle element is pivotably coupled to said curved region, whereby said handle can be selectively positioned between a protective orientation proximate the elongated member and a handle orientation distal from said elongated member.

19. A lancet device, comprising:

a housing having at least one exposed internal region:

a blade;

a drive mechanism for driving said blade from a fist position within said housing to a second position wherein said blade extends from said housing;

a handle element coupled to said housing, wherein said handle element is positionable between a first orientation, where said handle element substantially covers said exposed internal region, and a second orientation where said handle element protrudes as a handle from said housing.

\* \* \* \* \*